(12) United States Patent
Behr et al.

(10) Patent No.: US 10,487,764 B1
(45) Date of Patent: Nov. 26, 2019

(54) METHOD AND SYSTEM FOR CONTROLLING AN OXYGEN SENSOR

(71) Applicant: Ford Global Technologies, LLC, Dearborn, MI (US)

(72) Inventors: Kenneth Behr, Farmington Hills, MI (US); Zena Yanqing Yee, Beverly Hills, MI (US); Gladys Galicia, Shelby Township, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 14 days.

(21) Appl. No.: 15/988,440

(22) Filed: May 24, 2018

(51) Int. Cl.
*F02D 41/14* (2006.01)
*G01N 27/30* (2006.01)
*B60W 20/16* (2016.01)
*F02D 41/24* (2006.01)

(52) U.S. Cl.
CPC ......... *F02D 41/1494* (2013.01); *B60W 20/16* (2016.01); *F02D 41/1455* (2013.01); *F02D 41/2474* (2013.01); *G01N 27/30* (2013.01)

(58) Field of Classification Search
CPC .. F02D 41/14; F02D 41/1494; F02D 41/1455; F02D 41/2474; B60W 20/16; G01N 27/30
See application file for complete search history.

(56) References Cited

U.S. PATENT DOCUMENTS

| 6,253,542 | B1 * | 7/2001 | Omara ................ F02D 41/1441 123/339.12 |
| 6,382,015 | B1 | 5/2002 | Aoki |
| 10,001,045 | B2 * | 6/2018 | Kumar .................... F01N 3/101 |
| 2016/0103095 | A1 | 4/2016 | Surnilla et al. |

FOREIGN PATENT DOCUMENTS

CN 105697167 A 6/2016

\* cited by examiner

*Primary Examiner* — Hieu T Vo
(74) *Attorney, Agent, or Firm* — Geoffrey Brumbaugh; McCoy Russell LLP (57) ABSTRACT

Methods and systems are provided for adjusting a voltage of a heated oxygen sensor (HEGO) so that the heated oxygen sensor is controlled to a desired temperature as the HEGO ages. In one example, a method generates a requested heated oxygen sensor electrode impedance for control and then adjusts the voltage responsive to the requested heated oxygen sensor electrode impedance for control.

20 Claims, 9 Drawing Sheets

FIG. 7 the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

METHOD AND SYSTEM FOR CONTROLLING AN OXYGEN SENSOR

FIELD

The present description relates generally to controlling operation of an oxygen sensor as the oxygen sensor ages.

BACKGROUND/SUMMARY

An oxygen sensor may include a heater to operate the oxygen sensor within a desirable temperature range where output of the oxygen sensor may reliably reflect conditions within an exhaust system of an engine. If a voltage that is applied to the heater to control oxygen sensor temperature is too high or too low, output of the oxygen sensor may be less accurate than is desired. Consequently, an engine air-fuel ratio may be leaner or richer than is desired and conversion efficiency of exhaust after treatment devices may degrade. A voltage that is applied to the oxygen sensor's heater when the oxygen sensor is new to operate the oxygen sensor at a desired temperature may cause the same oxygen sensor to operate outside of a desired temperature range after the oxygen sensor has aged. Therefore, it may be desirable to provide a way of controlling oxygen sensor temperature so that the oxygen sensor operates in a desired temperature range even after the oxygen temperature sensor has aged.

The inventors herein have identified methods and systems that compensate for oxygen sensor electrode aging. In particular, the inventors have developed an operating method for an oxygen sensor, comprising: adjusting a voltage applied to an oxygen sensor heater while the oxygen sensor is exposed to combustion products of a first rich air-fuel mixture according to a first curve describing a relationship between oxygen sensor electrode impedance and oxygen sensor electrode temperature for the oxygen sensor being exposed to the combustion products of a second lean air-fuel mixture.

By adjusting a voltage applied to an oxygen sensor heater according to a first curve describing a relationship between oxygen sensor electrode impedance and oxygen sensor electrode temperature for the oxygen sensor being exposed to combustion products of a rich air fuel mixture, it is possible to provide the technical result of improved oxygen sensor temperature control. For example, the voltage that is applied to the oxygen sensor heater may be adjusted responsive to a requested oxygen sensor electrode impedance (Ri) for control, and the requested oxygen sensor electrode impedance (Ri) for control may be determined from curves describing relationships between oxygen sensor temperature and oxygen sensor electrode impedance during rich and lean exhaust gas conditions. As the oxygen sensor electrode impedance changes as the oxygen sensor ages, the requested oxygen sensor electrode impedance (Ri) for control may be revised so that the voltage applied to the oxygen sensor heater may be adjusted so as to operate the oxygen sensor electrode in a desired temperature range. As a result, the output of the oxygen sensor may be made more consistent as the oxygen sensor ages.

The present description may provide several advantages. In particular, the approach may improve engine air-fuel control and reduce engine emissions. Further, the approach does not require extensive oxygen sensor characterization to determine oxygen sensor operating characteristics at all stages of oxygen sensor life. Further still, the approach may be selectively activated to reduce controller computational load.

BRIEF DESCRIPTION OF THE DRAWINGS

FIGS. 6A-7 show flow charts of a method for operating a heated oxygen sensor (HEGO).

DETAILED DESCRIPTION

Figure 1:
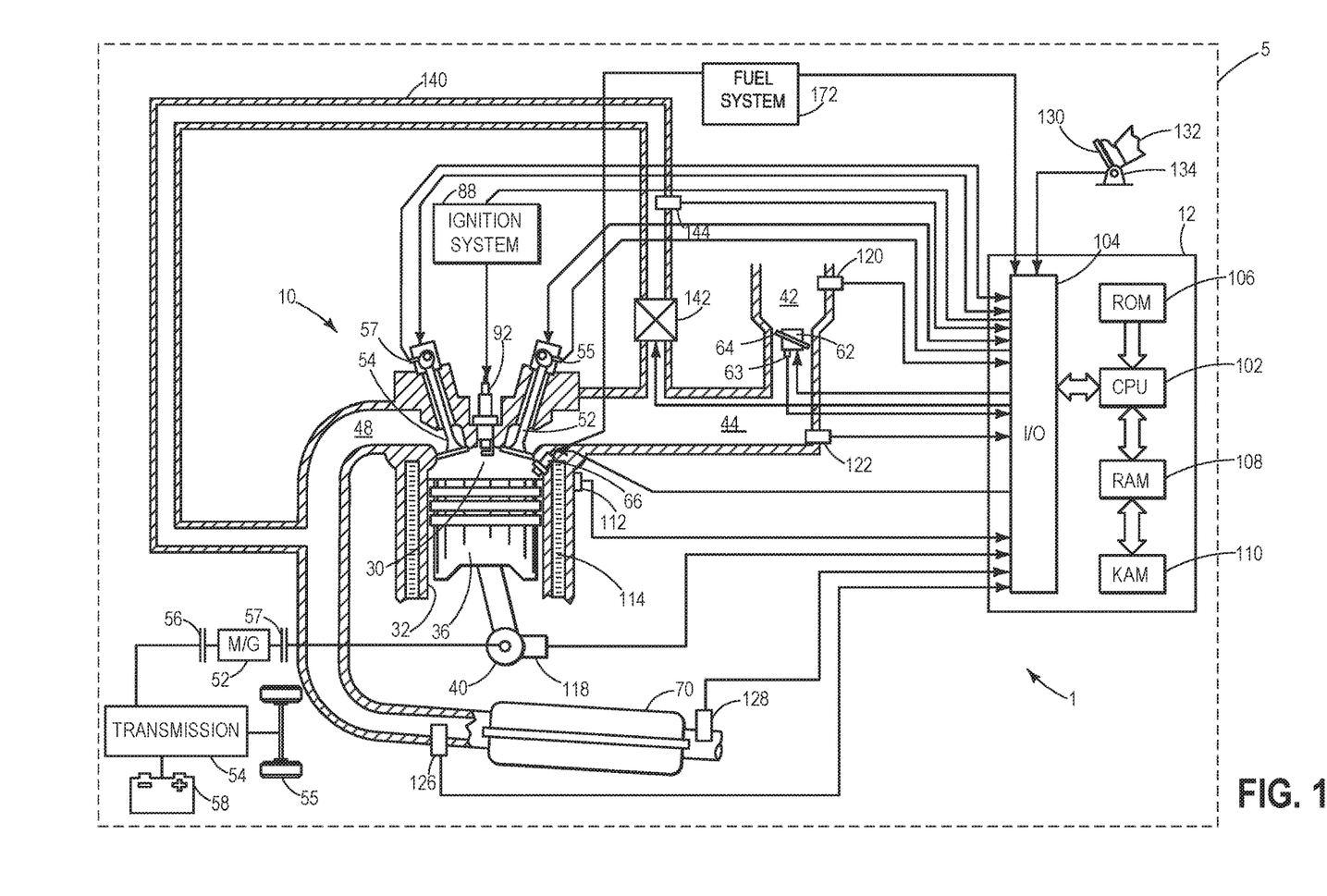
FIG. 1 shows a schematic depiction of an engine and an associated exhaust emissions system of a vehicle.
Figure 3:
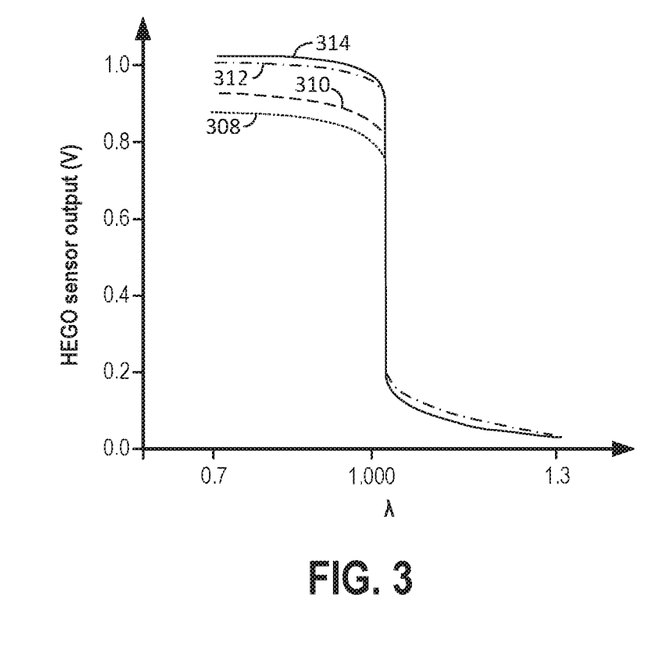
FIG. 3 shows how heated oxygen sensor output voltage changes as temperature of the heated oxygen sensor changes.
Figure 4:
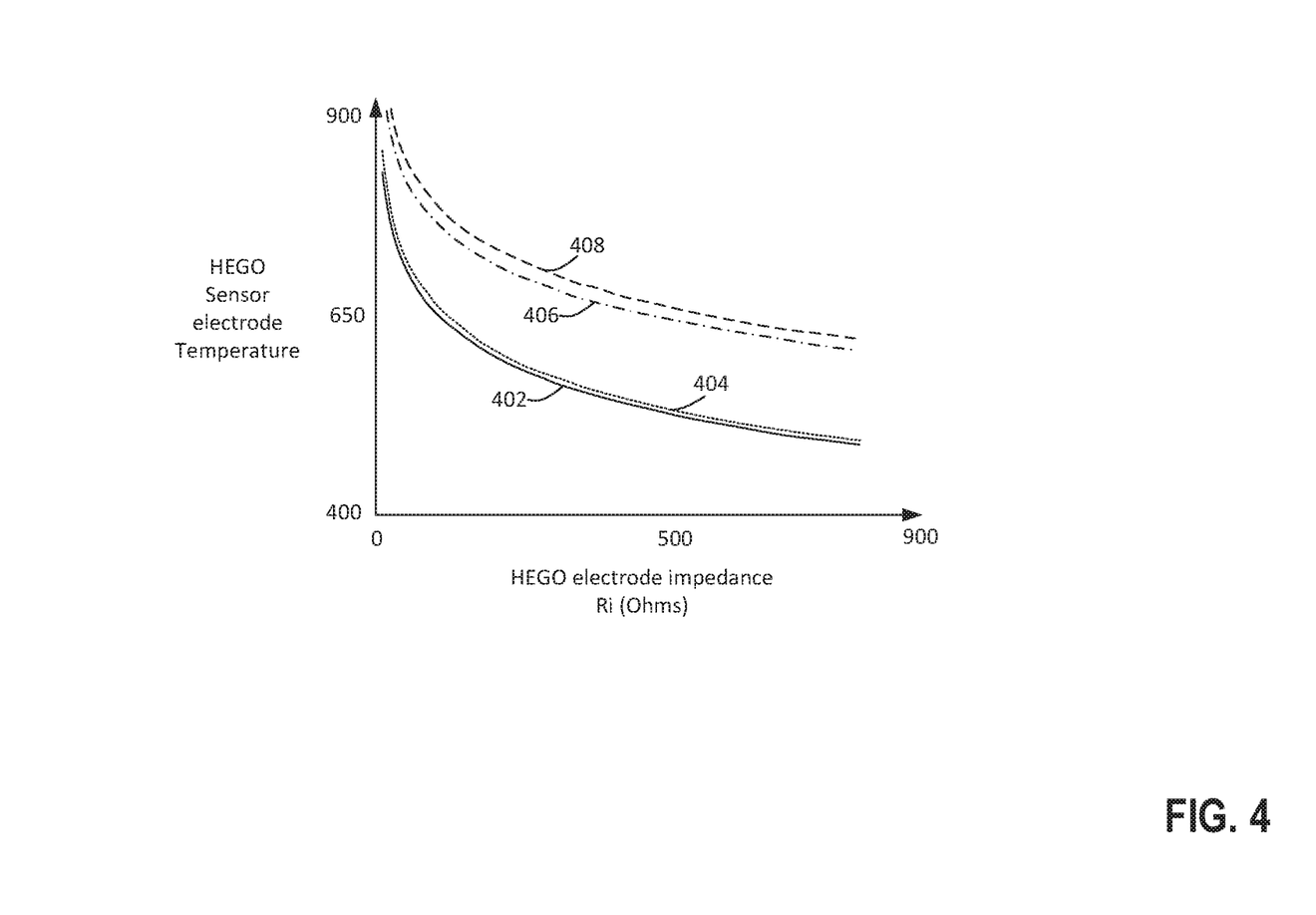
FIG. 4 shows example curves that describe relationships between oxygen sensor electrode temperature and oxygen sensor electrode impedance.
Figure 5:
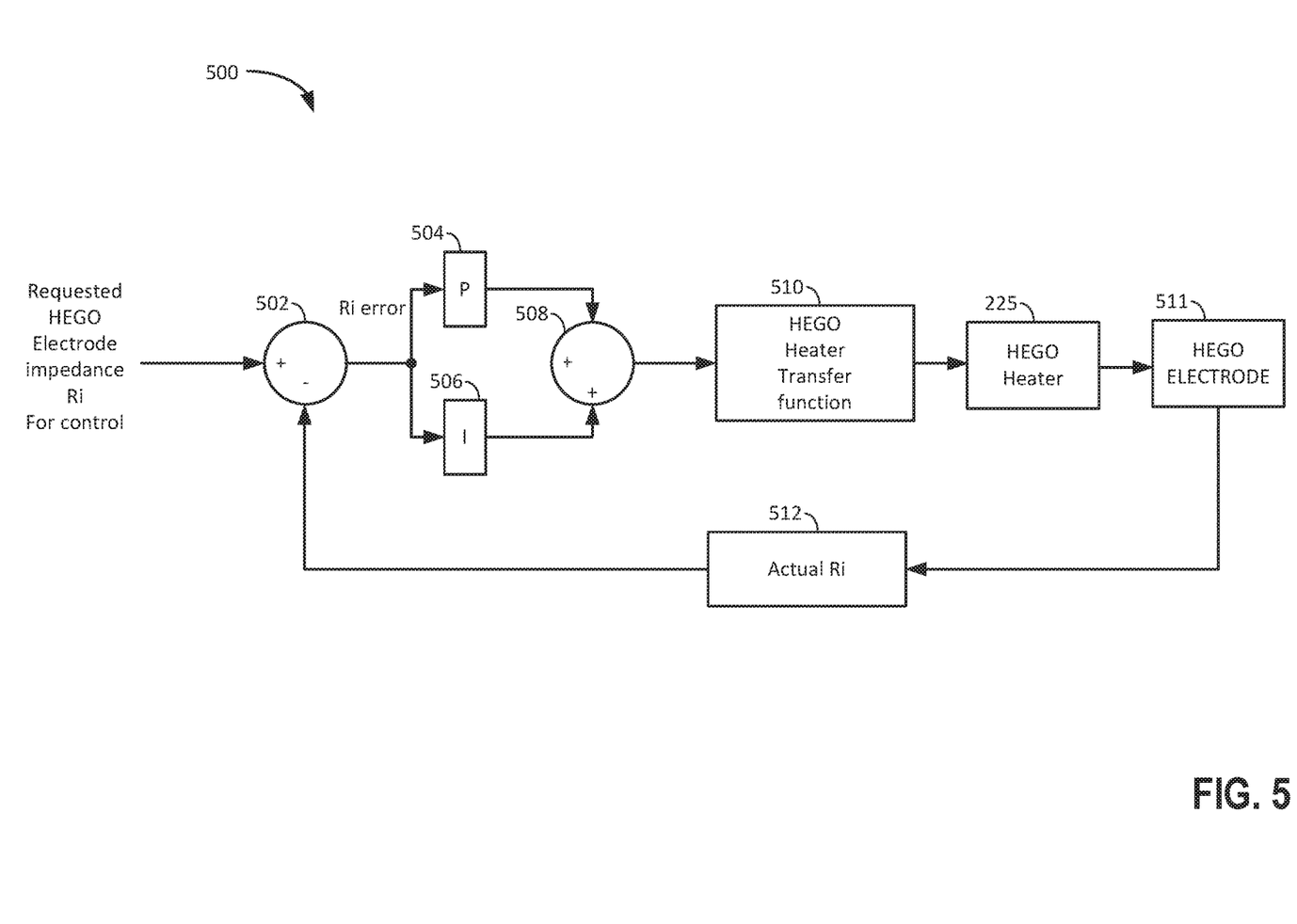
FIG. 5 shows a block diagram of a proportional/integral controller for an oxygen sensor.
Figure 7:
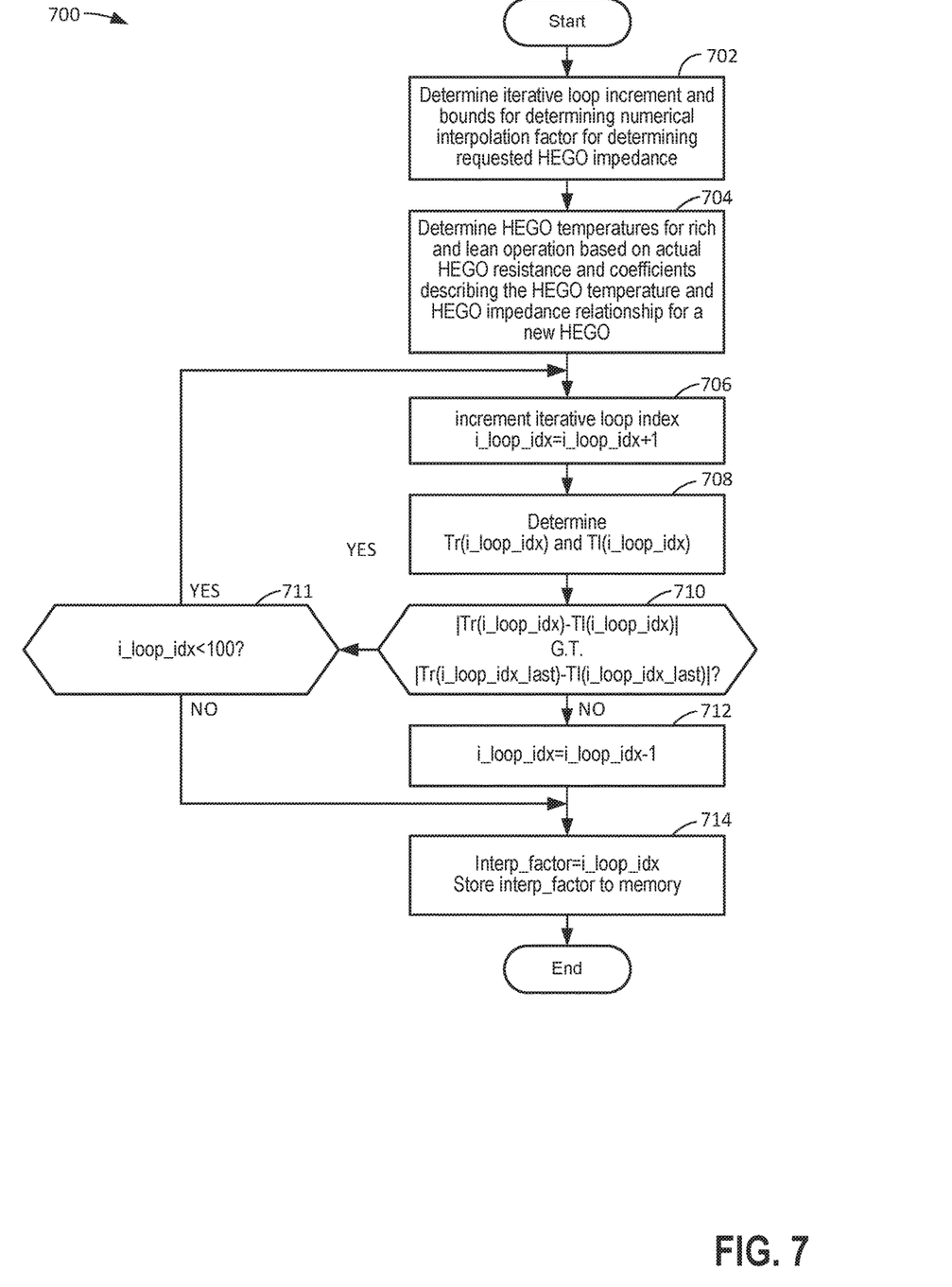
Figure 8:
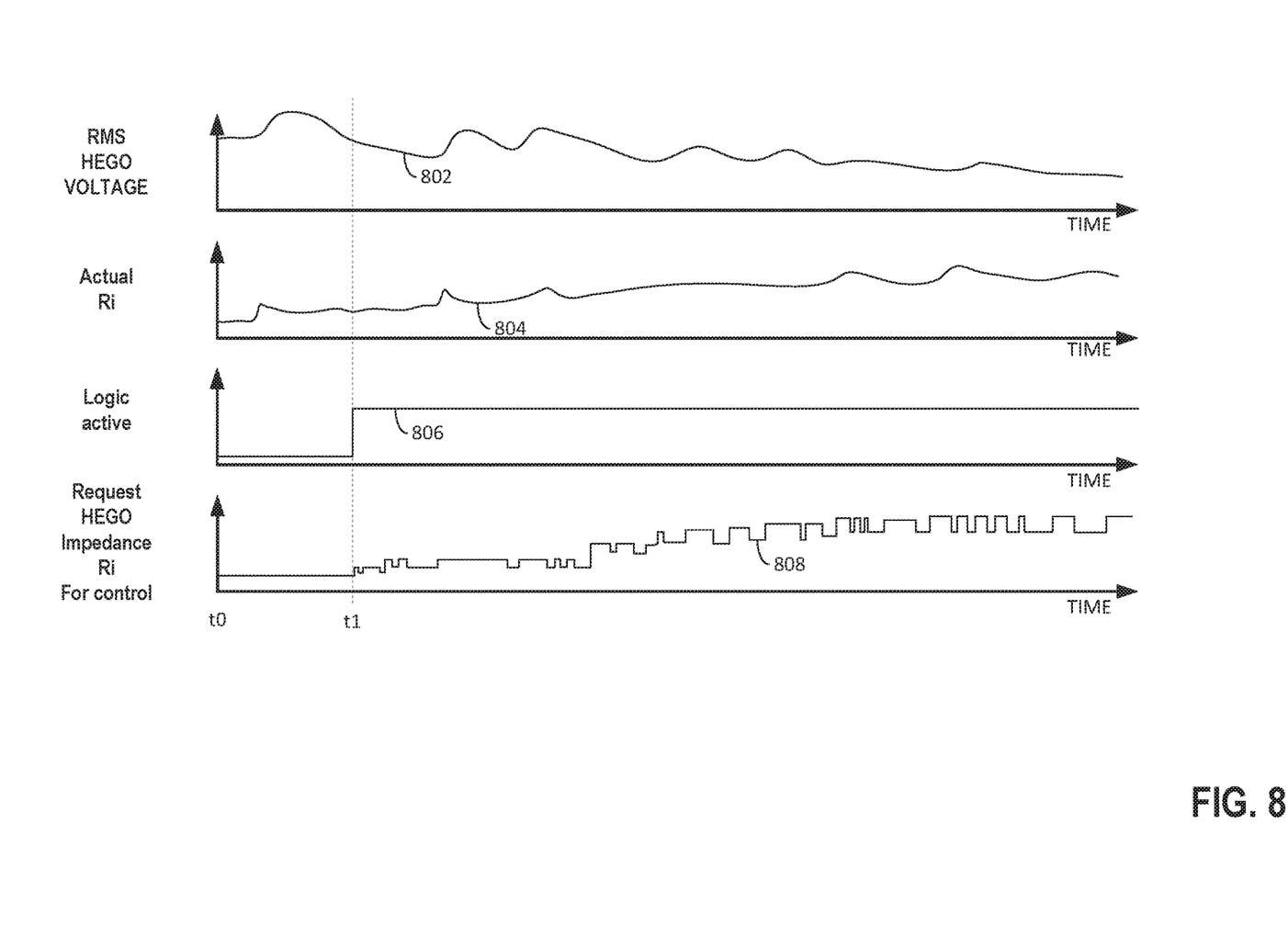
FIG. 8 shows an example HEGO operating sequence according to the method of FIGS. 6A-7.

The following description relates to systems and methods for operating a HEGO sensor. The HEGO sensor may be incorporated into a vehicle that includes an engine and exhaust system as shown in FIG. 1. The HEGO sensor may be of a type shown in FIG. 2 or of an alternative design. The HEGO sensor may have operating characteristics as shown in FIG. 3. The HEGO may have an electrode temperature to electrode resistance relationship as shown in FIG. 4. The vehicle may include a controller that includes a proportional/integral controller as shown in FIG. 5. The HEGO sensor may be operated according to the method of FIGS. 6A-7 to improve engine air-fuel control. The method of FIGS. 6A-7 may perform HEGO heater control as shown in FIG. 8.

Referring to FIG. 1, internal combustion engine 10, comprising a plurality of cylinders, one cylinder of which is shown in FIG. 1, is controlled by electronic engine controller 12. The controller 12 receives signals from the various sensors shown in FIGS. 1 and 2. Controller 12 employs the various actuators of FIGS. 1-2 to adjust engine and driveline operation based on the received signals and instructions stored on memory of controller 12. Engine 10 and electric machines described herein that provide torque to the vehicle driveline may be referred to as driveline torque sources.

Engine system 1 may be a propulsion system included in a motor vehicle 5. Engine 10 may be controlled at least partially by a control system including controller 12 and by input from a human vehicle operator 132 via an input device 130. In this example, input device 130 includes an accelerator pedal and a pedal position sensor 134 for generating a proportional pedal position signal. Combustion chamber (e.g., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle 55 via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some examples, combustion chamber 30 may include two or more intake valves and/or two more exhaust valves. In this example, intake valve 52 and exhaust valve 54 may be controlled by cam actuation via one or more cams and may utilize one or more of cam profile switching (CPS), variable cam timing (VCT), variable valve timing (VVT), and/or variable valve lift (VVL) systems that may be operated by controller 12 to vary valve operation. The position of intake valve 52 and exhaust valve 54 may be determined by position sensors 55 and 57, respectively. In alternative examples, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

In some examples, each cylinder of engine 10 may be configured with one or more fuel injectors for providing fuel thereto. As a non-limiting example, cylinder 30 is shown including one fuel injector 66, which is supplied fuel from fuel system 172. Fuel injector 66 is shown coupled directly to cylinder 30 for injecting fuel directly therein in proportion to a pulse width received from controller 12. In this manner, fuel injector 66 provides what is known as direct injection (hereafter also referred to as "DI") of fuel into combustion cylinder 30.

It will be appreciated that in an alternate example, injector 66 may be a port injector providing fuel into the intake port upstream of cylinder 30. It will also be appreciated that cylinder 30 may receive fuel from a plurality of injectors, such as a plurality of port injectors, a plurality of direct injectors, or a combination thereof.

Continuing with FIG. 1, intake passage 42 may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 via throttle position sensor 63. Intake passage 42 may include a mass air flow sensor 120 and a manifold air pressure sensor 122 for providing respective signals MAF and MAP to controller 12.

Ignition system 88 can provide an ignition spark to combustion chamber 30 via spark plug 92 in response to spark advance signal from controller 12, under select operating modes. Though spark ignition components are shown, in some examples, combustion chamber 30 or one or more other combustion chambers of engine 10 may be operated in a compression ignition mode, with or without an ignition spark.

An upstream exhaust gas sensor 126 is shown coupled to exhaust passage 48 upstream of emission control device 70. Upstream sensor 126 may be any suitable sensor for providing an indication of exhaust gas AFR such as a linear wideband oxygen sensor or UEGO; a two-state narrowband oxygen sensor or EGO; a HEGO; or a NOR, HC, or CO sensor. In the non-limiting examples described herein, upstream exhaust gas sensor 126 is a UEGO sensor configured to provide output, such as a voltage signal, that is proportional to the amount of oxygen present in the exhaust. Controller 12 uses the output to determine the exhaust gas AFR.

Emission control device 70 is shown arranged along exhaust passage 48 downstream of exhaust gas sensor 126. In the non-limiting examples describe herein, device 70 is a TWC configured to reduce $NO_x$ and oxidize CO and unburnt hydrocarbons. In other examples, however, device 70 may be a $NO_x$ trap, various other emission control devices, or combinations thereof.

A second, downstream exhaust gas sensor 128 is shown coupled to exhaust passage 48 downstream of emission control device 70. Downstream sensor 128 may be any suitable sensor for providing an indication of exhaust gas AFR such as a UEGO sensor, EGO sensor, HEGO sensor, etc. In the non-limiting examples described herein, downstream sensor 128 is a HEGO sensor configured to indicate the relative enrichment or enleanment of the exhaust gas after passing through the catalyst. The HEGO sensor may provide output in the form of a switch point, or the voltage signal at the point at which the exhaust gas switches from lean to rich.

Further, in the disclosed examples, an exhaust gas recirculation (EGR) system may route a desired portion of exhaust gas from exhaust passage 48 to intake passage 42 via EGR passage 140. The amount of EGR provided to intake passage 42 may be varied by controller 12 via EGR valve 142. Further, an EGR sensor 144 may be arranged within the EGR passage and may provide an indication of one or more of pressure, temperature, and concentration of the exhaust gas. Under some conditions, the EGR system may be used to regulate the temperature of the air and fuel mixture within the combustion chamber.

Controller 12 is shown in FIG. 1 as a microcomputer, including microprocessor unit 102, input/output ports 104, an electronic storage medium for executable programs and calibration values shown as read only memory chip 106 (non-transitory memory) in this particular example, random access memory 108, keep alive memory 110, and a data bus. Controller 12 may receive various signals from sensors coupled to engine 10 in addition to those signals previously discussed, including measurement of inducted mass air flow (MAF) from mass air flow sensor 120, engine coolant temperature (ECT) from temperature sensor 112 coupled to cooling sleeve 114, a profile ignition pickup signal (PIP) from Hall effect sensor 118 (or other type) coupled to crankshaft 40, throttle position (TP) from a throttle position sensor 63, absolute manifold pressure (MAP) signal from sensor 122, UEGO sensor output (UEGO) from UEGO sensor 126, and HEGO sensor output (HEGO) from HEGO sensor 128. An engine speed signal, RPM, may be generated by controller 12 from output of crankshaft position sensor 118.

Storage medium read-only memory 106 can be programmed with computer readable data representing non-transitory instructions executable by processor 102 for performing the methods described below as well as other variants that are anticipated but not specifically listed.

In some examples, vehicle 5 may be a hybrid vehicle with multiple sources of torque available to one or more vehicle wheels 55. In other examples, vehicle 5 is a conventional vehicle with only an engine, or an electric vehicle with only electric machine(s). In the example shown, vehicle 5 includes engine 10 and an electric machine 52. Electric machine 52 may be a motor or a motor/generator. Crankshaft 40 of engine 10 and electric machine 52 are connected via a transmission 54 to vehicle wheels 55 when one or more clutches 56 and 57 are engaged. In the depicted example, a first clutch 56 is provided between crankshaft 40 and electric machine 52, and a second clutch 57 is provided between electric machine 52 and transmission 54. Controller 12 may send a signal to an actuator of each clutch 56 and 57 to engage or disengage the clutches, so as to connect or disconnect crankshaft 40 from electric machine 52 and the components connected thereto, and/or connect or disconnect electric machine 52 from transmission 54 and the components connected thereto. Transmission 54 may be a gearbox, a planetary gear system, or another type of transmission. The powertrain may be configured in various manners including as a parallel, a series, or a series-parallel hybrid vehicle.

Electric machine 52 receives electrical power from a traction battery 58 to provide torque to vehicle wheels 55. Electric machine 52 may also be operated as a generator to provide electrical power to charge battery 58, for example during a braking operation.

As described above, FIG. 1 shows only one cylinder of a multi-cylinder engine, and each cylinder may similarly include its own set of intake/exhaust valves, fuel injector(s), spark plug(s), etc.

During operation, each cylinder within engine 10 typically undergoes a four stroke cycle: the cycle includes the intake stroke, compression stroke, expansion stroke, and exhaust stroke. During the intake stroke, generally, the exhaust valve 54 closes and intake valve 52 opens. Air is introduced into combustion chamber 30 via intake manifold 44, and piston 36 moves to the bottom of the cylinder so as to increase the volume within combustion chamber 30. The position at which piston 36 is near the bottom of the cylinder and at the end of its stroke (e.g. when combustion chamber 30 is at its largest volume) is typically referred to by those of skill in the art as bottom dead center (BDC). During the compression stroke, intake valve 52 and exhaust valve 54 are closed. Piston 36 moves toward the cylinder head so as to compress the air within combustion chamber 30. The point at which piston 36 is at the end of its stroke and closest to the cylinder head (e.g. when combustion chamber 30 is at its smallest volume) is typically referred to by those of skill in the art as top dead center (TDC). In a process hereinafter referred to as injection, fuel is introduced into the combustion chamber. In a process hereinafter referred to as ignition, the injected fuel is ignited by known ignition means such as spark plug 92, resulting in combustion. During the expansion stroke, the expanding gases push piston 36 back to BDC. Crankshaft 40 converts piston movement into a rotational torque of the rotary shaft. Finally, during the exhaust stroke, the exhaust valve 54 opens to release products of the combusted air-fuel mixture to exhaust manifold 48 and the piston returns to TDC. Note that the above is shown merely as an example, and that intake and exhaust valve opening and/or closing timings may vary, such as to provide positive or negative valve overlap, late intake valve closing, or various other examples. Engine torque may be adjusted via changing a position of one or more torque actuators (e.g., spark timing via ignition system 88, fuel injection amount via fuel injector 66, cam position via cam phase actuators).

Figure 2:
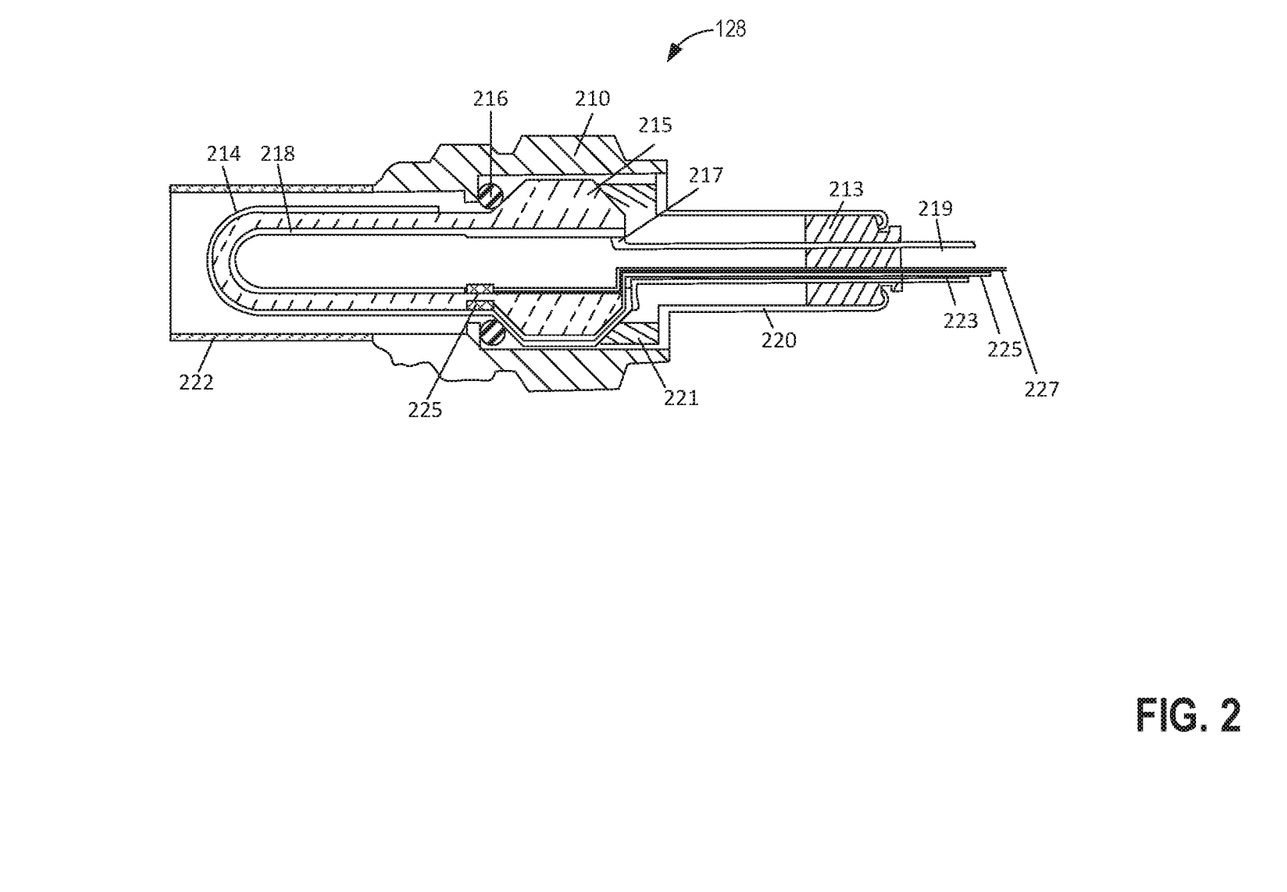
FIG. 2 shows a cross-section of a heated oxygen sensor.

FIG. 2 shows a cross section of an example HEGO sensor 128. The HEGO sensor 128 includes a $ZrO_2$ ceramic in the form of a hollow cylindrical tube 215 that is closed at one end. The $ZrO_2$ ceramic tube 215 has an exhaust gas electrode 214 and an outer surface and an air reference electrode 218 on an inner surface. Exhaust gas electrode 214 is made from a catalytic noble metal such as platinum. Air reference electrode 218 is made of a non-catalytic material and it contacts with output lead 219 through a conductor 217. Exhaust gas electrode 214 contacts output lead 223 through conductor 221. The $ZrO_2$ ceramic tube 215 is sealed onto an 18 mm annular spark plug shell 210 with a seal 216. Shell 210 has attached to one of its ends a cylindrical tube 220, which is closed off at the end with an electrically insulating cap 213. A protection tube 222 is attached on the other end of shell 210. The components of sensor 128 are substantially concentric around the axis of the sensor 128 except for internal conductors 217 and 221. Heater 225 is supplied electrical power via conductors 225 and 227, which are electrically coupled to controller 12 of FIG. 1.

The system of FIGS. 1 and 2 provides for a hybrid vehicle, comprising: a powertrain comprising an engine, a motor/generator, a battery, and a transmission coupled to vehicle wheels; a three-way catalyst arranged in an engine exhaust passage; a first heated exhaust gas oxygen (HEGO) sensor arranged downstream of the three-way catalyst in the exhaust passage; a second heated exhaust gas oxygen (HEGO) sensor arranged upstream of the three-way catalyst in the exhaust passage; a controller including non-transitory memory with instructions stored therein which are executable by the controller to: adjust a first voltage applied to a heater of the first HEGO responsive to a requested electrode impedance of the first HEGO, the requested electrode impedance generated via a first curve representing an aged oxygen sensor and a second curve representing a new oxygen sensor, and adjust a second voltage applied to a heater of the second HEGO responsive to a requested electrode impedance of the second HEGO, the requested electrode impedance generated via the first curve representing the aged oxygen sensor and the second curve representing the new oxygen sensor.

The hybrid vehicle further comprises additional instructions to generate a third curve based on the first curve, the second curve, and an actual electrode impedance of the HEGO. The hybrid vehicle includes where generating the third curve includes filtering a numerical interpolation factor that is a basis for generating the third curve. The hybrid vehicle further comprises additional instructions to iteratively determining the numerical interpolation factor. The hybrid vehicle further comprises additional instructions to determine an electrode impedance when the HEGO is exposed to exhaust gases of a combusted lean air-fuel mixture. The hybrid vehicle further comprises additional instructions to determine an electrode impedance when the HEGO is exposed to exhaust gases of a combusted rich air-fuel mixture.

FIG. 3 shows a plot illustrating how output voltage of a HEGO sensor changes as a temperature of the HEGO sensor changes. The vertical axis represents HEGO sensor output voltage and the horizontal axis represents air-fuel equivalence ratio (k), which is the engine air-fuel ratio divided by the stoichiometric air-fuel ratio for the fuel being combusted in the engine. Curve 308 represents HEGO sensor output when HEGO electrode temperature is 900° C. Curve 310 represents HEGO sensor output when HEGO electrode temperature is 750° C. Curve 312 represents HEGO sensor output when HEGO electrode temperature is 500° C. Curve 314 represents HEGO sensor output when HEGO electrode temperature is 400° C. The HEGO output voltages are equivalent when only curve 314 is visible.

It may be observed that the HEGO sensor output voltage changes with HEGO electrode temperature. Consequently, if engine air-fuel ratio is controlled responsive to HEGO sensor output without consideration of HEGO sensor temperature, the engine's air fuel ratio may be adjusted to an undesirable air-fuel ratio. However, if HEGO electrode temperature may be maintained at a nearly constant at a desired temperature (e.g., 650° C.), then HEGO sensor output voltage may be made more consistent so that engine air-fuel ratio may be controlled more accurately.

Referring now to FIG. 4, a plot showing relationships between HEGO sensor electrode temperature and HEGO sensor electrode impedance (Ri) are shown. The vertical axis represents HEGO sensor electrode temperature. The horizontal axis represents HEGO sensor electrode resistance. Curve 402 represents a relationship between HEGO sensor electrode impedance and HEGO sensor electrode temperature when the HEGO sensor is exposed to exhaust gases of a combusted lean air-fuel mixture when the HEGO sensor is new. Curve 404 represents a relationship between HEGO sensor electrode impedance and HEGO sensor electrode temperature when the HEGO sensor is exposed to exhaust gases of a combusted rich air-fuel mixture when the HEGO sensor is new. Curve 406 represents a relationship between HEGO sensor electrode impedance and HEGO sensor electrode temperature when the HEGO sensor is exposed to exhaust gases of a combusted lean air-fuel mixture when the HEGO sensor is aged (e.g., operated in a vehicle for several years). Curve 408 represents a relationship between HEGO sensor electrode impedance and HEGO sensor electrode temperature when the HEGO sensor is exposed to exhaust gases of a combusted rich air-fuel mixture when the HEGO sensor is aged.

It may be observed that for a particular HEGO temperature, impedance of the HEGO electrode increases for an aged HEGO sensor as compared to a new HEGO sensor for conditions when the HEGO is exposed to combustion gases from lean and rich air-fuel mixtures. In addition, curves 402 and 404 are nearly identical, but there is significant separation between curves 406 and 408. As such, the HEGO sensor electrode impedance when the HEGO sensor is exposed to lean exhaust gas conditions may be different than the HEGO sensor electrode impedance when the HEGO is exposed to rich exhaust conditions for a same HEGO temperature. Therefore, it may be desirable to determine the HEGO sensor electrode impedance when the HEGO sensor is exposed to combustion products of a lean air-fuel ratio and HEGO sensor electrode impedance when the HEGO sensor is exposed to combustion products of a rich air-fuel ratio so that HEGO electrode temperature may be controlled more accurately.

The HEGO electrode impedance (e.g., impedance between the air reference electrode and the exhaust gas electrode) may change over time due to a platinum electrode of the HEGO sensor partially separating from the $ZrO_2$ ceramic. The HEGO sensor electrode impedance may increase over time, and because a voltage applied to the HEGO heater voltage is based on the HEGO sensor electrode impedance, the HEGO heater voltage may be improperly adjusted if the change to HEGO sensor electrode impedance is not compensated. The output voltage of the HEGO sensor may be described by Nernst equation:

$$V = \frac{RT}{4F} \ln\left(\frac{P_{atm}}{P_{ex}}\right)$$

where V is the HEGO sensor output voltage, R is the gas constant, T is the absolute temperature of HEGO sensor electrode, ln is the natural log function, $P_{atm}$ is the partial pressure of oxygen in the atmosphere, and $P_{ex}$ is the partial pressure of oxygen in the exhaust gas being sensed via the HEGO sensor.

Curve 402 may be described by the equation:

HEGO_Elec_TEMP_LEAN_$N$=$AL\_n$·ln(actual_HEGO_IMP_LEAN)+$BL\_n$ where HEGO_Elec_Temp_LEAN_N is the HEGO electrode temperature in ° C. for when the HEGO is new and exposed to exhaust gases of a combusted lean air-fuel mixture, AL_n is a value of a first constant for describing a curve for when the HEGO is new and exposed to exhaust gases of a combusted lean air-fuel mixture, ln is the natural log function, actual_HEGO_IMP_LEAN is the actual HEGO electrode impedance measured when the HEGO was exposed to exhaust gases of a combusted lean air-fuel mixture, and BL_n is a second constant for describing the curve for when the HEGO is new and exposed to exhaust gases of a combusted lean air-fuel mixture. The requested HEGO impedance (Ri) for control may be determined for a given HEGO electrode temperature when constants AL_n and BL_n for describing the curve that relates HEGO electrode temperature to HEGO electrode impedance are known via the following equation:

$$\text{HEGO\_Ri\_CTL} = e^{\frac{(\text{HEGO\_Elec\_TEMP} - \text{BL\_n})}{\text{AL\_n}}}$$

where e is Euler's number≈2.71828, and where the other variables are as previously described.

Curve 404 may be described by the equation:

HEGO_Elec_TEMP_RICH_$N$=$AR\_n$·ln(actual_HEGO_IMP_RICH)+$BR\_n$ where HEGO_Elec_Temp_RICH_N is the HEGO electrode temperature in ° C. for when the HEGO is new and exposed to exhaust gases of a combusted rich air-fuel mixture, AR_n is a value of a first constant for describing a curve for when the HEGO is new and exposed to exhaust gases of a combusted rich air-fuel mixture, ln is the natural log function, actual_HEGO_IMP_RICH is the actual HEGO electrode impedance measured when the HEGO was exposed to exhaust gases of a combusted rich air-fuel mixture, and BR_n is a second constant for describing a curve for when the HEGO is new and exposed to exhaust gases of a combusted rich air-fuel mixture.

Curve 406 may be described by the equation:

HEGO_Elec_TEMP_LEAN_$A$=$AL\_a$·ln(actual_HEGO_IMP_LEAN)+$BL\_a$ where HEGO_Elec_Temp_LEAN_A is the HEGO electrode temperature in ° C. for when the HEGO is aged and exposed to exhaust gases of a combusted lean air-fuel mixture, AL_a is a value of a first constant for describing a curve for when the HEGO is aged and exposed to exhaust gases of a combusted lean air-fuel mixture, ln is the natural log function, actual_HEGO_IMP_LEAN is the actual HEGO electrode impedance measured when the HEGO was exposed to exhaust gases of a combusted lean air-fuel mixture, and BL_a is a second constant for describing a curve for when the HEGO is aged and exposed to exhaust gases of a combusted lean air-fuel mixture.

Curve 408 may be described by the equation:

$$\text{HEGO\_Elec\_TEMP\_RICH\_}A = AR\_a \cdot \ln(\text{actual\_HEGO\_IMP\_RICH}) + BR\_a$$

where HEGO_Elec_Temp_RICH_A is the HEGO electrode temperature in ° C. for when the HEGO is aged and exposed to exhaust gases of a combusted rich air-fuel mixture, AR_a is a value of a first constant for describing a curve for when the HEGO is aged and exposed to exhaust gases of a combusted rich air-fuel mixture, ln is the natural log function, actual_HEGO_IMP_RICH is the actual HEGO electrode impedance measured when the HEGO was exposed to exhaust gases of a combusted rich air-fuel mixture, and BR_a is a second constant for describing a curve for when the HEGO is aged and exposed to exhaust gases of a combusted rich air-fuel mixture.

The values of AL_a, BL_a, AL_n, BL_n, AR_a, BR_a, AR_n, and BR_n may be determined via measuring HEGO impedance and temperature when the HEGO is exposed to lean and rich gases of combusted lean and rich air-fuel mixtures. The values may be stored in controller memory and used as a basis for solving requested HEGO impedance values for control as discussed in the description of FIGS. 6A-7.

Referring now to FIG. 5, a block diagram of an example proportional/integral controller 500 for controlling voltage output to a HEGO sensor is shown. The HEGO heater generates thermal energy to heat the HEGO sensor when a voltage is supplied to the HEGO sensor heater.

A requested HEGO electrode impedance Ri for control is input into summing junction 502. The initial value of the requested HEGO electrode impedance Ri for control may be a predetermined value of HEGO electrode impedance when the HEGO sensor is new and at 650° C. The initial requested HEGO electrode impedance Ri for control may be stored in controller memory.

From time-to-time a measurement of the actual HEGO electrode impedance is measured via controller 12 of FIG. 1. The actual HEGO electrode impedance is input to the minus input of summing junction 502 so that the output of summing junction 502 is a HEGO electrode impedance error. The HEGO electrode impedance error is then provided to block 504 where it is multiplied by a predetermined value (e.g., a scalar that is the proportional gain) such that the output of block 504 is proportionate to the HEGO electrode impedance error. The HEGO electrode impedance error is also input into block 506 where it is integrated and where it may also be multiplied by a scalar (e.g., the integral gain). The outputs of blocks 504 and 506 are input to summing junction 508 where they are added together. The output of summing junction 508 is input to block 510 where it is multiplied by a scalar that has units of volts/Ohm and converted into a voltage output via controller 12 of FIG. 1. The voltage output from block 510 is then applied to HEGO heater 225. The HEGO heater heats the HEGO electrode and electrode impedance is measured via controller 12 of FIG. 1 to determine the actual HEGO electrode impedance Ri at block 512.

In this way, actual HEGO electrode impedance and requested HEGO electrode impedance for control may be the basis for applying a voltage to a HEGO heater. The HEGO electrode impedance for control may be determined as discussed in the description of FIGS. 6A-7.

Figure 6A:
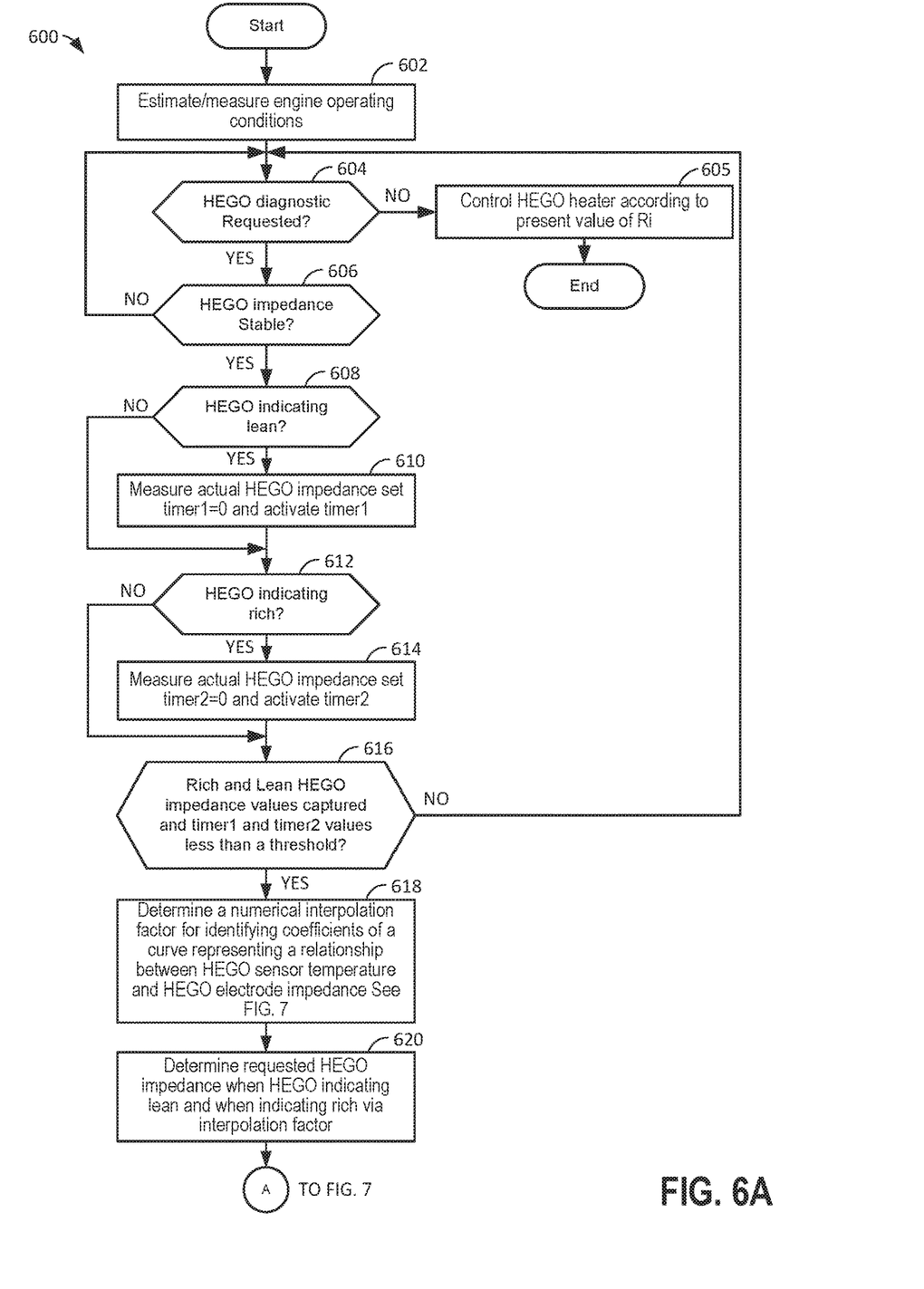
Figure 6B:
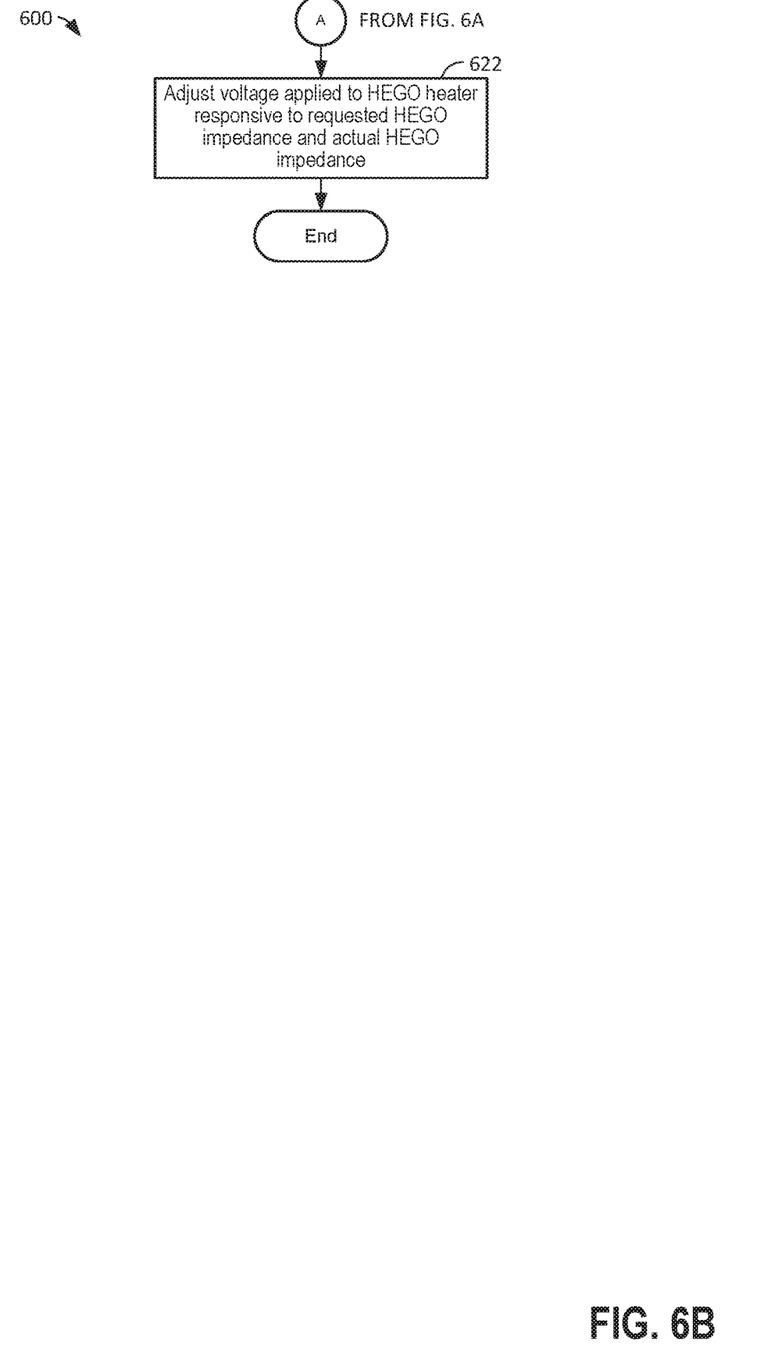

Referring now to FIGS. 6A and 6B, a method for operating a HEGO sensor is shown. The method of FIGS. 6A and 6B may be at least partially implemented as executable instructions stored in non-transitory controller memory. The method of FIGS. 6A and 6B may cooperate with and be a part of the system of FIGS. 1 and 2. At least portions of the method of FIGS. 6A and 6B may be actions taken in the physical world via controller 12 to transform operating conditions of a vehicle. Further, the method of FIGS. 6A, 6B, and 7 along with the system of FIGS. 1 and 2 may provide the sequence shown in FIG. 8. The method of FIGS. 6A, 6B, and 7 may be applied to oxygen sensors that are upstream and downstream of a three-way catalyst as shown in FIG. 1.

At 602, method 600 determines engine operating conditions. Engine operating conditions may include but are not limited to engine speed, engine torque, engine temperature, engine air-fuel ratio, ambient temperature, and a distance traveled by the vehicle since the most recent engine start. Method 600 proceeds to 604.

At 604, method 600 judges if HEGO diagnostics are requested. HEGO diagnostics may be requested each time the vehicle is driven after the HEGO sensor reaches a predetermined temperature (e.g., 650° C.). In addition, additional conditions may be required to initiate HEGO diagnostics. For example, engine temperature may be required to be greater than a threshold temperature, engine speed may have to be changing by less than a predetermined amount (e.g., 500 RPM/minute), and engine air-fuel ratio may have to be changing by less than a predetermined amount (e.g., 1.2 air-fuel ratios per minute). If method 600 judges that conditions are present to initiate HEGO diagnostics, the answer is yes, method 600 proceeds to 606, and HEGO diagnostics are requested. Otherwise, the answer is no, HEGO diagnostics are not requested, and method 600 proceeds to 605.

At 605, method 600 controls a voltage applied to a HEGO heater responsive to a present value of requested HEGO electrode impedance (Ri) for control. The voltage may be applied to the HEGO heater via a proportional/integral controller as shown in FIG. 5. The requested HEGO electrode impedance (Ri) for control may be retrieved from memory and input to the proportional/integral controller. Method 600 proceeds to exit after adjusting voltage that is applied to the HEGO heater.

At 606, method 600 judges if conditions are present for stable HEGO electrode impedance values. In one example, method 600 may sample and measure HEGO electrode impedance values a plurality of times. If the measured HEGO electrode impedance values are not zero, two HEGO electrode impedance values that have been measured over a predetermined amount of time are within a threshold value, HEGO electrode temperature is greater than a threshold, and an amount of time that voltage has been applied to the HEGO heater exceeds a threshold, then the answer is yes and method 600 proceeds to 608. Otherwise, the answer is no and method 600 returns to 604.

At 608, method 600 judges if the HEGO sensor is indicating that it is exposed to lean exhaust gases in the engine exhaust system (e.g., HEGO output voltage less than 0.2 volts). If so, the answer is yes and method 600 proceeds to 610. Otherwise, the answer is no and method 600 proceeds to 612.

At 610, method 600 samples and measures the actual HEGO electrode impedance via controller 12 of FIG. 1. Method 600 also resets a value of timer1 to zero and allows timer1 to count up in time. The measured actual HEGO electrode impedance is stored in controller memory as variable actual_HEGO_IMP_LEAN. Method 600 proceeds to 612.

At 612, method 600 judges if the HEGO sensor is indicating that it is exposed to rich exhaust gases in the engine exhaust system (e.g., HEGO output voltage greater than 0.45 volts). If so, the answer is yes and method 600 proceeds to 614. Otherwise, the answer is no and method 600 proceeds to 616.

At 614, method 600 samples and measures the actual HEGO electrode impedance via controller 12 of FIG. 1. Method 600 also resets a value of timer2 to zero and allows timer2 to count up in time. The measured actual HEGO electrode impedance is stored in controller memory as variable actual_HEGO_IMP_RICH. Method 600 proceeds to 616.

At 616, method 600 judges if a HEGO impedance value has been measured while the HEGO was exposed solely to exhaust gases that are a product of combustion of a lean air-fuel mixture and if a HEGO impedance value has been measured while the HEGO was exposed solely to exhaust gases that are a product of combustion of a rich air-fuel mixture. Further, method 600 judges if the two HEGO impedance values were measured while the values of timer1 and timer2 are less than a threshold amount of time. If two HEGO impedance measurements were taken, one during rich exhaust conditions and one during lean exhaust conditions, while the values of timer1 and timer2 are less than a threshold, then the answer is yes and method 600 proceeds to 618 to identify aging of the HEGO sensor. Otherwise, the answer is no and method 600 returns to 604. By returning to 604, method 600 may make several attempts to sample and measure HEGO electrode impedance while the HEGO is exposed to lean and rich exhaust gases.

At 618, method 600 determines a numerical interpolation factor for identifying coefficients that describe a curve representing a relationship between HEGO electrode temperature and HEGO electrode impedance. The numerical interpolation factor is determined as discussed in the description of FIG. 7. Method 600 proceeds to 620.

At 620 method 600 determines a requested HEGO electrode impedance (Ri) for control for when the HEGO is exposed to exhaust gases of a combusted lean air-fuel ratio. Method 600 also determines a requested HEGO impedance (Ri) for control when the HEGO is exposed to exhaust gases of a combusted rich air-fuel ratio.

The requested HEGO impedance (Ri) for control when the HEGO is exposed to exhaust gases of a combusted rich air-fuel mixture may be determined for a given HEGO electrode temperature (e.g., 650° C.) when constants AR_n, AR_a, BR_n, and BR_a are known via the following equation:

$$\text{HEGO\_Ri\_CTL\_R} = e^{\frac{\left(650°\ C.-\left(BR\_n+\left(\left(\frac{Interp\_factor}{100}\right)\cdot(BR\_a-BR\_n)\right)\right)\right)}{\left(AR\_n+\left(\left(\frac{Interp\_factor}{100}\right)\cdot(AR\_a-AR\_n)\right)\right)}}$$

where e is Euler's number≈2.71828, and where the other variables are as previously described. The values of AR_n, AR_a, BR_n, and BR_a are retrieved from controller memory as mentioned in the description of FIG. 4 and 650° C. is the desired operating temperature for the HEGO sensor.

The requested HEGO impedance (Ri) for control when the HEGO is exposed to exhaust gases of a combusted lean air-fuel mixture may be determined for a given HEGO electrode temperature (e.g., 650° C.) when constants AR_n, AR_a, BR_n, and BR_a are known via the following equation:

$$\text{HEGO\_Ri\_CTL\_L} = e^{\frac{\left(650°\ C.-\left(BL\_n+\left(\left(\frac{Interp\_factor}{100}\right)\cdot(BL\_a-BL\_n)\right)\right)\right)}{\left(AL\_n+\left(\left(\frac{Interp\_factor}{100}\right)\cdot(AL\_a-AL\_n)\right)\right)}}$$

The values of AR_n, AR_a, BR_n, and BR_a are retrieved from controller memory as mentioned in the description of FIG. 4 and 650° C. is the desired operating temperature for the HEGO sensor. Method 600 proceeds to 622.

At 622, method 600 adjusts a voltage that is applied to the HEGO heater responsive to the requested HEGO impedance (Ri) values for control (e.g., HEGO_Ri_CTL_L and HEGO_Ri_CTL_R) and the actual HEGO impedance values (e.g., actual_HEGO_IMP_LEAN and actual_HEGO_IMP_RICH). In particular, when the HEGO is exposed to exhaust gases of combusted rich air-fuel mixtures, the variables HEGO_Ri_CTL_R and actual_HEGO_IMP_RICH are input to a proportional/integral controller described in FIG. 5, and the proportional/integral controller outputs a voltage to the HEGO heater. Similarly, when the HEGO is exposed to exhaust gases of combusted lean air-fuel mixtures, the variables HEGO_Ri_CTL_L and actual_HEGO_IMP_LEAN are input to a proportional/integral controller described in FIG. 5, and the proportional/integral controller outputs a voltage to the HEGO heater. Method 600 proceeds to exit.

In this way, a voltage applied to a HEGO heater may be adjusted to compensate changes in HEGO electrode impedance. The compensation also is unique for the HEGO being exposed to exhaust gases of combusted lean air-fuel mixtures and for the HEGO being exposed to exhaust gases of combusted lean air-fuel mixtures. The method of FIGS. 6A-7 iteratively interpolates between values of coefficients that describe relationships between HEGO electrode temperature and HEGO electrode impedance for HEGO sensors that are exposed to exhaust gases of combusted lean and rich air-fuel mixtures.

At 702, method 700 determines an iterative loop increment and bounds for determining a numerical interpolation factor. The numerical interpolation factor is a basis for determining the requested HEGO electrode impedance (Ri) for control. In one example, the iterative loop increment is a value of one and one hundred steps may be taken between values of coefficients that describe different relationships between HEGO electrode temperature and HEGO electrode impedance. A variable i_loop_idx represents an iterative loop index that keeps track of how many times the loop between step 708 and step 712 is executed. Thus, if a first curve representing relationship between HEGO electrode temperature and HEGO impedance for a new HEGO sensor that is exposed to exhaust gases of a combusted lean air-fuel mixture is described by AL_n=−78.62 and BL_n=1011.8, and a second curve representing relationship between HEGO electrode temperature and HEGO impedance for an aged HEGO sensor that is exposed to exhaust gases of a combusted lean air-fuel mixture is described by AL_a=−77.57 and BL_a=1051.9, then the increment size between AL coefficients is (−77.57+78.62)/100 and the increment size between BL coefficients is (1051.9−1011.8)/100. The values of AL_a, AL_n, BL_a, and BL_n define the bounds for determining coefficients of a curve that describes the HEGO at its present age when exposed to exhaust gases of a combusted lean air-fuel mixture. However, it is also possible to extrapolate beyond the bounds of the AL_a, AL_n, BL_a, and BL_n coefficients if desired. Thus, coefficients describing curves as shown in FIG. 4 are the basis for determining coefficients describing curves representing relationships between HEGO electrode temperature and HEGO electrode impedance for the HEGO at its present age for a HEGO that is exposed to exhaust gases of combusted rich and lean air-fuel mixtures. Method 700 proceeds to 704.

At 704, method 700 determines temperatures for conditions when the HEGO is new and exposed to exhaust of lean and rich combusted air-fuel mixtures. In particular, method 700 solves the following equations:

HEGO_Elec_TEMP_LEAN_$N$($i$_loop_idx)=$AL\_n$·ln(actual_HEGO_IMP_LEAN)+$BL\_n$

HEGO_Elec_TEMP_RICH_$N$($i$_loop_idx)=$AR\_n$·ln(actual_HEGO_IMP_RICH)+$BR\_n$

The variables are defined as previously discussed with regard to FIG. 4 and the values of HEGO_Elec_TEMP_LEAN_N(i_loop_idx) and HEGO_Elec_TEMP_RICH_N(i_loop_idx) are stored to controller memory, where i_loop_idx=i_loop_idx_last=0. Method 700 proceeds to 706.

At 706, method 700 increments the iterative loop index i_loop_idx by the loop increment value of one. Method 700 proceeds to 708.

At 708, method 700 solves the following equations:

$$\text{HEGO\_Elec\_TEMP\_LEAN\_N(i\_loop\_idx)} =$$
$$AL\_n + \left(\frac{i\_loop\_idx}{100} \cdot (AL\_a - AL\_n)\right) \cdot \ln(\text{actual\_HEGO\_IMP\_LEAN}) + \left(BL\_n + \left(\left(\frac{i\_loop\_idx}{100}\right) \cdot (BL\_a - BL\_n)\right)\right)$$

$$\text{HEGO\_Elec\_TEMP\_RICH\_N(i\_loop\_idx)} =$$
$$AR\_n + \left(\frac{i\_loop\_idx}{100} \cdot (AR\_a - AR\_n)\right) \cdot \ln(\text{actual\_HEGO\_IMP\_RICH}) + \left(BR\_n + \left(\left(\frac{i\_loop\_idx}{100}\right) \cdot (BR\_a - BR\_n)\right)\right)$$

The values of $\left(AL\_n + \left(\frac{i\_loop\_idx}{100} \cdot (AL\_a - AL\_n)\right)\right)$ and $\left(BL\_n + \left(\left(\frac{i\_loop\_idx}{100}\right) \cdot (BL\_a - BL\_n)\right)\right)$ are coefficients describing a curve that has been interpolated from curves representing new and aged HEGO sensors operating in lean exhaust conditions. Likewise, the values of $$AR\_n + \left(\frac{i\_loop\_idx}{100} \cdot (AR\_a - AR\_n)\right) \text{ and}$$
$$\left(BR\_n + \left(\left(\frac{i\_loop\_idx}{100}\right) \cdot (BR\_a - BR\_n)\right)\right)$$

are coefficients describing a curve that has been interpolated from curves representing new and aged HEGO sensors operating in rich exhaust conditions. Method 700 then proceeds to 710.

At 710, method 700 judges if the following conditions are true.

|HEGO_Elec_TEMP_RICH($i$_loop_idx)−HEGO_Elec_TEMP_LEAN($i$_loop_idx)|>|HEGO_Elec_TEMP_RICH($i$_loop_idx_last)−HEGO_Elec_TEMP_LEAN($i$_loop_idx_last)|

Thus, method 700 judges if a temperature difference between a HEGO electrode exposed to exhaust gases of a combusted rich air-fuel mixture and the HEGO electrode being exposed to exhaust gases of a combusted lean air-fuel mixture for the present value of the iterative loop index i_loop_idx is greater than a temperature difference between a HEGO electrode exposed to exhaust gases of a combusted rich air-fuel mixture and the HEGO electrode being exposed to exhaust gases of a combusted lean air-fuel mixture for the last value of the iterative loop index i_loop_idx_last. If so, the answer is yes and method 700 proceeds to 711 because the temperature difference between a HEGO electrode exposed to exhaust gases of a combusted rich air-fuel mixture and the HEGO electrode being exposed to exhaust gases of a combusted lean air-fuel mixture is decreasing. As such, the temperature difference is being minimized so that a best fit value of the numerical interpolation factor (Interp_factor) may be determined. If not, the answer is no and method 700 proceeds to 712 because the temperature difference between a HEGO electrode exposed to exhaust gases of a combusted rich air-fuel mixture and the HEGO electrode being exposed to exhaust gases of a combusted lean air-fuel mixture is increasing.

At 711, method 700 judges if the value of the loop index i_loop_idx is less than 100 (e.g., the number of steps between coefficient values). If so, the answer is yes and method 700 returns to 706. In addition, the present value of variable i_loop_idx is stored to the variable i_loop_idx_last so that the comparison at 710 may be made. If not, the answer is no and method 700 proceeds to 714.

At 712, method 700 subtracts a value of one from the value of variable i_loop_idx so that the value of i_loop_idx corresponds to the minimum value of |HEGO_Elec_TEMP_RICH(i_loop_idx)−HEGO_Elec_TEMP_LEAN(i_loop_idx)|. Method 700 proceeds to 714.

At 714, method 700 equates the value of the numeric interpolation factor Interp_factor to the value of the interpolation loop index value i_loop_idx or Interp_factor=i_loop_idx. Method 700 stores the value of Interp_factor to controller memory and exits. In some examples, the value of Interp_factor may be low pass filtered via a software filter before it is stored to controller memory so that interpolating between the curves describing the relationship between HEGO electrode temperature and HEGO electrode impedance may advance the value of Interp_factor slower over time.

Thus, the method of FIGS. 6A-7 provide for an operating method for an oxygen sensor, comprising: adjusting a voltage applied to an oxygen sensor heater while the oxygen sensor is exposed to combustion products of a first rich air-fuel mixture according to a first curve describing a relationship between oxygen sensor electrode impedance and oxygen sensor temperature for the oxygen sensor being exposed to the combustion products of a second rich air-fuel mixture. The method further comprises adjusting the voltage applied to the oxygen sensor heater while the oxygen sensor is exposed to combustion products of a first lean air-fuel mixture according to a second curve describing a relationship between oxygen sensor electrode impedance and oxygen sensor temperature for the oxygen sensor being exposed to the combustion products of a second lean air-fuel mixture. The method includes where the first curve is derived from a third curve (e.g., curve 408) describing a relationship between oxygen sensor electrode impedance and oxygen sensor temperature for an aged oxygen sensor being exposed to combustion products of the second rich air-fuel mixture and a fourth curve (e.g., curve 404) describing a relationship between oxygen sensor electrode impedance and oxygen sensor temperature for a new oxygen sensor being exposed to combustion products of the second rich air-fuel mixture. The method includes where the second curve is derived from a fifth curve (e.g., curve 406) describing a relationship between oxygen sensor electrode impedance and oxygen sensor temperature for the aged oxygen sensor being exposed to combustion products of the second lean air-fuel mixture and a sixth curve (e.g., curve 402) describing a relationship between oxygen sensor electrode impedance and oxygen sensor temperature for a new oxygen sensor being exposed to combustion products of the second lean air-fuel mixture.

In some examples, the method further comprising subtracting an actual oxygen sensor electrode impedance from a requested oxygen sensor electrode impedance to adjust the voltage applied to the oxygen sensor heater. The method includes where the first curve is described via a first numeric coefficient and a second numeric coefficient. The method includes where the second curve is described via a first numeric coefficient and a second numeric coefficient. The method includes where the voltage is adjusted during conditions when the oxygen sensor impedance is determined to be stable.

The method described herein also provides for an operating method for an oxygen sensor, comprising: adjusting a requested oxygen sensor electrode impedance while the oxygen sensor is exposed to combustion products of a first rich air-fuel mixture according to a first curve describing a relationship between oxygen sensor electrode impedance and oxygen sensor temperature for the oxygen sensor being exposed to the combustion products of a second rich air-fuel mixture; and adjusting a voltage applied to a heater of the oxygen sensor according to the requested oxygen sensor electrode impedance. The method further comprises subtracting actual oxygen sensor electrode impedance from the requested oxygen sensor electrode impedance to generate an oxygen sensor electrode impedance error. The method further comprises modifying the electrode impedance error via proportional and integral controller gains to generate a proportional and integral controller output. The method further comprises adjusting the voltage applied to a heater of the oxygen sensor responsive to the proportional and integral controller output.

In some examples, the method further comprises adjusting the requested oxygen sensor electrode impedance while the oxygen sensor is exposed to combustion products of a first lean air-fuel mixture according to a second curve describing a relationship between oxygen sensor electrode impedance and oxygen sensor temperature for the oxygen sensor being exposed to the combustion products of a second lean air-fuel mixture. The method further comprising interpolating between a third curve and a fourth curve to generate the first curve.

Referring now to FIG. 8, an example HEGO heater control sequence for the system of FIGS. 1 and 2 according to the method of FIGS. 6A-7 is shown. The vertical line at time t1 indicates a time of interest during the sequence.

The first plot from the top of FIG. 8 is a plot root-mean-square (RMS) voltage applied to a HEGO sensor heater to control HEGO electrode temperature to improve HEGO sensor output. The vertical axis represents RMS voltage applied to the HEGO heater and RMS voltage increases in the direction of the vertical axis arrow. The horizontal axis represents time and time increases from the left side of the figure to the right side of the figure. Trace 802 represents RMS voltage applied to the HEGO heater.

The second plot from the top of FIG. 8 is a plot of measured actual HEGO sensor electrode impedance versus time. The vertical axis represents actual HEGO sensor impedance and actual HEGO sensor impedance increases in the direction of the vertical axis arrow. The horizontal axis represents time and time increases from the left side of the figure to the right side of the figure. Trace 804 represents the actual HEGO electrode impedance.

The third plot from the top of FIG. 8 is a plot of a state of logic to adjust the requested HEGO electrode impedance for control versus time. The vertical axis represents the state of state of logic to adjust the requested HEGO electrode impedance for control and the value of the requested HEGO electrode impedance for control is adjusted when trace 806 is at a higher level near the vertical axis arrow. The requested HEGO electrode impedance for control is not adjusted when trace 806 is at a lower level near the horizontal axis. Trace 806 represents the state of state of logic to adjust the requested HEGO electrode impedance for control. The horizontal axis represents time and time increases from the left side of the figure to the right side of the figure.

The fourth plot from the top of FIG. 8 is a plot of requested HEGO sensor electrode impedance for control versus time. The vertical axis represents requested HEGO sensor impedance for control and requested HEGO sensor impedance for control increases in the direction of the vertical axis arrow. The horizontal axis represents time and time increases from the left side of the figure to the right side of the figure. Trace 808 represents the requested HEGO electrode impedance for control.

At time $t_0$, the RMS voltage that is applied to the HEGO heater is at a high level since the actual HEGO electrode impedance is low. The logic to adjust the requested HEGO electrode impedance Ri for control is not activated and the requested HEGO electrode impedance Ri for control value is low.

At time t1, the logic to adjust the requested HEGO electrode impedance Ri for control is activated and the requested HEGO electrode impedance Ri for control value is still low. However, as the actual HEGO sensor electrode impedance is increased, the requested HEGO electrode impedance is increased according to the method of FIGS. 6A-7. This causes the RMS voltage that is applied to the HEGO heater to be reduced. By reducing the RMS voltage that is applied to the HEGO heater, the HEGO electrode temperature may be maintained at a desired level.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example examples described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific examples are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A hybrid vehicle, comprising:
a powertrain comprising an engine, a motor/generator, a battery, and a transmission coupled to vehicle wheels;
a three-way catalyst arranged in an engine exhaust passage;
a first heated exhaust gas oxygen (HEGO) sensor arranged downstream of the three-way catalyst in the exhaust passage;
a second HEGO sensor arranged upstream of the three-way catalyst in the exhaust passage;
a controller including non-transitory memory with instructions stored therein which are executable by the controller to:
adjust a first voltage applied to a heater of the first HEGO responsive to a requested electrode impedance of the first HEGO, the requested electrode impedance generated via a first curve representing an aged oxygen sensor and a second curve representing a new oxygen sensor, and adjust a second voltage applied to a heater of the second HEGO responsive to a requested electrode impedance of the second HEGO, the requested electrode impedance generated via the first curve representing the aged oxygen sensor and the second curve representing the new oxygen sensor.

2. The hybrid vehicle of claim 1, further comprising additional instructions to generate a third curve based on the first curve, the second curve, and an actual electrode impedance of the HEGO.

3. The hybrid vehicle of claim 1, where generating the third curve includes filtering a numerical interpolation factor that is a basis for generating the third curve.

4. The hybrid vehicle of claim 3, further comprising additional instructions to iteratively determining the numerical interpolation factor.

5. The hybrid vehicle of claim 1, further comprising additional instructions to determine an electrode impedance when the HEGO is exposed to exhaust gases of a combusted lean air-fuel mixture.

6. The hybrid vehicle of claim 1, further comprising additional instructions to determine an electrode impedance when the HEGO is exposed to exhaust gases of a combusted rich air-fuel mixture.

7. An operating method for an oxygen sensor, comprising:
adjusting a voltage applied to an oxygen sensor heater while the oxygen sensor is exposed to combustion products of a first rich air-fuel mixture according to a first curve describing a relationship between oxygen sensor electrode impedance and oxygen sensor temperature for the oxygen sensor being exposed to the combustion products of a second rich air-fuel mixture.

8. The method of claim 7, further comprising:
adjusting the voltage applied to the oxygen sensor heater while the oxygen sensor is exposed to combustion products of a first lean air-fuel mixture according to a second curve describing a relationship between oxygen sensor electrode impedance and oxygen sensor temperature for the oxygen sensor being exposed to the combustion products of a second lean air-fuel mixture.

9. The method of claim 8, where the first curve is derived from a third curve describing a relationship between oxygen sensor electrode impedance and oxygen sensor temperature for an aged oxygen sensor being exposed to combustion products of the second rich air-fuel mixture and a fourth curve describing a relationship between oxygen sensor electrode impedance and oxygen sensor temperature for a new oxygen sensor being exposed to combustion products of the second rich air-fuel mixture.

10. The method of claim 9, where the second curve is derived from a fifth curve describing a relationship between oxygen sensor electrode impedance and oxygen sensor temperature for the aged oxygen sensor being exposed to combustion products of the second lean air-fuel mixture and a sixth curve describing a relationship between oxygen sensor electrode impedance and oxygen sensor temperature for a new oxygen sensor being exposed to combustion products of the second lean air-fuel mixture.

11. The method of claim 8, where the second curve is described via a first numeric coefficient and a second numeric coefficient.

12. The method of claim 7, further comprising subtracting an actual oxygen sensor electrode impedance from a requested oxygen sensor electrode impedance to adjust the voltage applied to the oxygen sensor heater.

13. The method of claim 7, where the first curve is described via a first numeric coefficient and a second numeric coefficient.

14. The method of claim 7, where the voltage is adjusted during conditions when the oxygen sensor impedance is determined to be stable.

15. An operating method for an oxygen sensor, comprising:
adjusting a requested oxygen sensor electrode impedance while the oxygen sensor is exposed to combustion products of a first rich air-fuel mixture according to a first curve describing a relationship between oxygen sensor electrode impedance and oxygen sensor temperature for the oxygen sensor being exposed to the combustion products of a second rich air-fuel mixture; and
adjusting a voltage applied to a heater of the oxygen sensor according to the requested oxygen sensor electrode impedance.

16. The method of claim 15, further comprising subtracting an actual oxygen sensor electrode impedance from the requested oxygen sensor electrode impedance to generate an oxygen sensor electrode impedance error.

17. The method of claim 16, further comprising modifying the electrode impedance error via proportional and integral controller gains to generate a proportional and integral controller output.

18. The method of claim 17, further comprising adjusting the voltage applied to a heater of the oxygen sensor responsive to the proportional and integral controller output.

19. The method of claim 15, further comprising adjusting the requested oxygen sensor electrode impedance while the oxygen sensor is exposed to combustion products of a first lean air-fuel mixture according to a second curve describing a relationship between oxygen sensor electrode impedance and oxygen sensor temperature for the oxygen sensor being exposed to the combustion products of a second lean air-fuel mixture.

20. The method of claim 15, further comprising interpolating between a third curve and a fourth curve to generate the first curve.

\* \* \* \* \*